(12) United States Patent
Scott

(10) Patent No.: US 7,775,085 B2
(45) Date of Patent: Aug. 17, 2010

(54) HIGH WATER CUT WELL MEASUREMENTS WITH HYDRO-SEPARATION

(75) Inventor: Bentley N. Scott, Garland, TX (US)

(73) Assignee: Phase Dynamics, Inc., Richardson, TX (US)

(*) Notice: Subject to any disclaimer, the term of this patent is extended or adjusted under 35 U.S.C. 154(b) by 712 days.

(21) Appl. No.: 11/522,846

(22) Filed: Sep. 18, 2006

(65) Prior Publication Data

US 2007/0240498 A1 Oct. 18, 2007

Related U.S. Application Data

(60) Provisional application No. 60/792,528, filed on Apr. 17, 2006.

(51) Int. Cl.
*G01N 33/28* (2006.01)

(52) U.S. Cl. .................. 73/61.43; 73/61.44; 73/61.45; 73/61.49

(58) Field of Classification Search ............... 73/61.43, 73/61.44, 61.45, 61.49
See application file for complete search history.

(56) References Cited

U.S. PATENT DOCUMENTS

| | | | |
|---|---|---|---|
| 4,852,395 A * | 8/1989 | Kolpak | 73/61.44 |
| 5,001,434 A * | 3/1991 | Marrelli et al. | 324/640 |
| 5,259,239 A | 11/1993 | Gaisford | |
| 5,260,667 A | 11/1993 | Garcia-Golding et al. | |
| 5,576,974 A | 11/1996 | Marrelli et al. | |
| 5,654,502 A | 8/1997 | Dutton | |
| 6,234,030 B1 | 5/2001 | Butler | |
| 6,318,156 B1 | 11/2001 | Dutton et al. | |
| 6,327,914 B1 | 12/2001 | Dutton | |
| 2005/0081643 A1 | 4/2005 | Mattar et al. | |

* cited by examiner

*Primary Examiner*—Daniel S Larkin

(57) ABSTRACT

Methods and systems for determining the water, oil, and gas fractions in hydrocarbons from high water cut hydrocarbon wells. A hydrocarbon flow stream discharging from a well is subjected to hydro-separation to produce an oil-enriched fractional stream upon which water content measurements can be more accurately and reproducibly made. Calculations based on the water content of the oil-enriched fractional stream and the flow rate of at least one of the streams through the separator are conducted to determine the water content of the original stream. This provides a simple approach to measuring the water content in high water cut hydrocarbons that is real-time, accurate, and reproducible.

7 Claims, 8 Drawing Sheets

Figure 1C

Hydro-Separator Flow Balance Using a 2 Inch Hydroclone

| COLUMN | A<br>% Water Cut | B<br>Total Flow Volume, cubic meters/day | C<br>Water Flow Volume, cubic meters/day | D<br>Oil Flow Volume, cubic meters/day | E<br>Inner Diameter of Hydroclone, meters | F<br>Outer Diameter of Hydroclone, meters | G<br>Outer Annular Cross Sectional Area of Hydroclone, sq meters | H<br>Inner Circular Cross Sectional Area of Hydroclone, sq. meters | I<br>Total Cross Sectional Area of Hydroclone, sq. meters | L<br>Hydro-Separated Annular (More Dense) Water-Phase Flow Volume, cubic meters/day | M<br>Hydro-Separated Enriched (Less Dense) Oil Phase Flow Volume, cubic meters/day | N<br>% Water Cut of Enriched (Less Dense) Oil Phase |
|---|---|---|---|---|---|---|---|---|---|---|---|---|
| STREAM REFERENCE NUMBER IN FIGURE 1 | 104 | 104 | 104 | 104 | N/A | N/A | N/A | N/A | N/A | 106 | 108 | 108 |
| Example 1 | 98% | 200 | 196 | 4 | 0.0254 | 0.0508 | 0.00152 | 0.00051 | 0.00203 | 150.0 | 50.0 | 92% |
| Example 2 | 95% | 200 | 190 | 10 | 0.0254 | 0.0508 | 0.00152 | 0.00051 | 0.00203 | 150.0 | 50.0 | 80% |
| Example 3 | 93% | 200 | 186 | 14 | 0.0254 | 0.0508 | 0.00152 | 0.00051 | 0.00203 | 150.0 | 50.0 | 72% |
| Example 4 | 92% | 200 | 184 | 16 | 0.0254 | 0.0508 | 0.00152 | 0.00051 | 0.00203 | 150.0 | 50.0 | 68% |
| Example 5 | 90% | 200 | 180 | 20 | 0.0254 | 0.0508 | 0.00152 | 0.00051 | 0.00203 | 150.0 | 50.0 | 60% |
| Example 6 | 80% | 200 | 160 | 40 | 0.0254 | 0.0508 | 0.00152 | 0.00051 | 0.00203 | 150.0 | 50.0 | 20% |

Hydro-Separator Flow Balance Using 3 Inch Hydrocyclone

| Example 7  | 98% | 200 | 196 | 4  | 0.0254 | 0.0762 | 0.00405 | 0.00051 | 0.0046 | 177.8 | 22.2 | 82% |
| Example 8  | 95% | 200 | 190 | 10 | 0.0254 | 0.0762 | 0.00405 | 0.00051 | 0.0046 | 177.8 | 22.2 | 55% |
| Example 9  | 93% | 200 | 186 | 14 | 0.0254 | 0.0762 | 0.00405 | 0.00051 | 0.0046 | 177.8 | 22.2 | 37% |
| Example 10 | 92% | 200 | 184 | 16 | 0.0254 | 0.0762 | 0.00405 | 0.00051 | 0.0046 | 177.8 | 22.2 | 28% |
| Example 11 | 90% | 200 | 180 | 20 | 0.0254 | 0.0762 | 0.00405 | 0.00051 | 0.0046 | 177.8 | 22.2 | 10% |

HIGH WATER CUT WELL MEASUREMENTS WITH HYDRO-SEPARATION

CROSS-REFERENCE TO RELATED APPLICATIONS

This application claims priority from U.S. Provisional Patent application 60/792,528 filed on Apr. 17, 2006, which is hereby incorporated by reference.

BACKGROUND AND SUMMARY OF THE INVENTION

The present application relates generally to systems and methods for characterizing a multiphase fluid flow stream which has varying phase proportions over time, and in particular to improved systems and methods for measuring the amount of water in crude petroleum oil flowing from a high water cut hydrocarbon production well.

The following paragraphs contain some discussion which is illuminated by the innovations disclosed in this application, and any discussion of actual or proposed or possible approaches in these paragraphs does not imply that those approaches are prior art.

Background: Production and Analysis of High Water Cut Crude Petroleum Oil

Crude petroleum oil and gaseous hydrocarbons are produced by extracting them from subterranean reservoirs. Sometimes the oil and gas flows to the surface due to the natural pressure when a well is first drilled. Often, however, other methods are required to bring them, and particularly the oil, to the surface. These include a variety of techniques including driving the reservoir with injection water. A water-drive reservoir can produce a crude petroleum oil as an oil and water mixture, with water content percentages as high as 99% to just under 100% water. Note that in the petroleum industry, the water fraction in oil is known as the water cut ("WC") and the oil fraction is referred to as the oil cut ("OC").

The need for a very accurate determination of the water cut of crude petroleum oil is important during the taxation of crude petroleum oil and the sale of crude petroleum oil, where the owner or seller of the oil does not want to pay taxes on water, and the customer or buyer does not want to pay the price of oil for water. Thus, multiple determinations and cross-checks are often conducted on-line and off-line during petroleum production.

The offline method involves physically sampling the stream and analyzing it in a laboratory setting. In the petroleum industry, the sampling is usually done using a composite sampler which automatically opens a sample valve attached to a pipeline at some frequency to collect an aggregate sample into a sample container. The objective is to collect a sample which is representative of the production period of petroleum under consideration. After collection, the composite sample is usually picked-up by a person and taken to a laboratory. The composite sample is then "sampled" to prepare aliquots, or sub-divisions of the composite sample, for each of the various measurements, or analysis methods, to be used. However, in the case of high water cut wells, composite samplers are not routinely used because the sample is so high in water content that it is difficult, for example, to get a representative aliquot from the composite sample. Thus, the aliquot preparation itself introduces significant uncertainty into water cut determinations from high water cut wells.

Three off-line analytical methods are commonly used for determining the water content of crude petroleum oil, if a representative sample can be obtained to analyze. These are the centrifuge method, the distillation method, and the titration method. See the American Petroleum Institute ("API") Manual of Petroleum Measurement Standards, Chapter 10. However, the API standardized methods for testing crude petroleum oil do not apply to samples with water cuts above 2%. Thus, they are not applicable to high water cut wells.

Regarding on-line methods, one method involves the use of test separator vessels. This approach generally uses a tank sized to attempt to continuously separate the well output into two or three streams, such as a gas stream, a water stream, and an oil stream, and then separately meter each stream. The Petroleum Engineering Handbook, $3^{rd}$ Printing, from the Society of Petroleum Engineers, Richardson, Tex., Howard B. Bradley, editor-in-chief, 1992, describes such separators in Chapter 12, and is hereby incorporated by reference. However, the method of using test separators has several drawbacks including susceptibility to not being able to separate emulsions of oil and water, large holdup volume of water and hydrocarbon, and large physical footprint.

A major problem exists when using such separator vessel methods when the water cut is consistently above 80% and in the water continuous phase. In many cases, the only measure of oil production is obtained by producing a given well directly into a static storage tank, to allow for settling and separation of the oil and water phases as a "batch", until the volume of oil is significant enough for liquid level measurements to be made. In the usual mode, the tank is allowed to fill, and then the liquid levels of oil and water are measured by gauging the tank with a tape measure using weights to lower the tape into the liquid mixture. Specifically, a water/oil interface-indicating material is placed on the tape measure to determine the height of the water-oil interface. The total height of the liquid level is also measured. Then, the height measurements for each phase are related back to the volume calibration table, known as the strapping table, for that particular vessel. For example, if the batch settling tank employed is shaped as a right cylinder with a flat bottom, then the heights of each settled layer, i.e. the water phase layer and the oil phase layer, are a measure of water cut. For example, if a 99% water cut oil is being produced and the right cylinder tank is filled and settled to 100 inches in height, then the oil layer will be one inch thick. This approach is very coarse, and involves personnel and dedication of one tank to the measurement of each well. This routine is also very time-consuming as most high water wells produce fluids and oil at a very reduced rate.

Accordingly, the use of rapid on-line instruments such as densitometers, capacitance probes, radio frequency probes, and microwave analyzers to measure water content of petroleum products is becoming more common to solve such problems. Additionally, on-line measurements of, for example, physical and electrical properties, via instrumentation reduces the need human involvement in the process of measuring the composition of crude petroleum oil.

Background: Water Cut by the Density and Electromagnetic Characterization Methods On-line densitometers can be used to ascertain the amount of water in petroleum oil. One on-line density method uses a Coriolis meter. This meter can be installed in the pipeline leaving the well or wells. Coriolis meters measure the density of a fluid or fluid mixture, and usually its mass flow rate as well, using the Coriolis effect. Then, calculations can be performed to indirectly determine the water cut. For example, a Coriolis meter can measure the density of a water-oil mixture, $\rho_{mixture}$, and then perform a simple calculation to determine the individual fractions, or cuts, of the water phase and oil phase. By knowing or assuming the density of the dry oil, $\rho_{dry\ oil}$, and the density of the water phase, $\rho_{water\ phase}$, then a water weight percentage, $\psi_{water}$, can be calculated as follows:

$$\psi_{water\ phase} = ((\rho_{mixture} - \rho_{dry\ oil})/(\rho_{water\ phase} - \rho_{dry\ oil})) \times 100$$

Note that the above equation can work equally well using the specific gravities of the mixture, dry oil, and water phase, where specific gravity is the ratio of the particular density to the density of water at four degrees Celsius.

It should be recognized that the water cut by the density method is subject to uncertainty. First, due to natural variations of, for example, the hydrocarbon composition of crude petroleum oil, the density of the dry oil can vary significantly from the assumed or inputted value required for the simple calculation. Such a value is inputted into a densitometer based on an estimate or on the history of a given hydrocarbon well or field. Crude petroleum oils can range from about 800 kilograms per cubic meter ($kg/m^3$) to about 995 $kg/m^3$. Further, the water encountered in hydrocarbon well production is most often saline. This salinity is subject to variability, ranging from about 0.1% by weight "salts" to about 28%. This results in a variation in the density of the water phase from about 1001 $kg/m^3$ to about 1200 $kg/m^3$. Again, this value would be inputted into a densitometer based on an estimate or on the history of a given well or oil field.

A further problem with high water cut oils and using density as a measure of the water cut is the "closeness" of the oil and water densities. This prevents an accurate measurement, even if the exact densities of the dry oil and pure water phase are known at the operating temperature and pressure. The error quickly exceeds 20% of the measurement at 70% water and grows larger as the water cut increases. To illustrate, consider the uncertainty associated with measuring the water cut of a 99% water cut oil using densitometry. For example, if the true exact density of the pure saline water phase is 1050 $kg/m^3$, and the true exact density of the dry oil is 950 $kg/m^3$, the true density of a 99% water cut oil will be 1049 $kg/m^3$. Further assume that the density of the mixture can be measured to an accuracy of plus or minus 0.1% about the true value, which is a total uncertainty ("uncertainty band") of 0.2%. This amount of uncertainty equates to about 2 $kg/m^3$ units (0.002 times 1049 $kg/m^3$ equals 2.098 $kg/m^3$) which is larger than the true difference between the pure water phase and the true density of a 99% water cut oil, given the assumptions above. In practice, this means that the densitometer is incapable of distinguishing a 99% water cut oil from the pure water. Thus, densitometers presented with high water cut oils with close densities between the oil phase and water phase face significant challenges in accurately measuring the water cuts, or even being able to measure the water cut.

Another on-line instrument technique to determine the water cut of a crude petroleum oil is to use a microwave analyzer, instead of a densitometer, to perform the in-line monitoring of the oil and water mixture. The technique is referred to as water cut by electromagnetic measurement.

U.S. Pat. No. 4,862,060 to Scott (the '060 patent), entitled Microwave Apparatus for Measuring Fluid Mixtures and which is hereby incorporated by reference, discloses microwave apparatuses and methods which are suitable for monitoring water cuts when the water is dispersed in a continuous oil phase.

Note that the change in fluid mixture dielectric properties for a water and oil mixture can be affected by a number of parameters, including not only the percentage of water in oil, but also the individual dielectric constants of the oil phase and the water phase. For example, the dielectric constant of the dry crude petroleum oil itself can vary depending on its density and chemical composition. Note that temperature can affect the density of the oil and the water and thus the dielectric properties of each component and the mixture. However, temperature variations can easily be compensated for by using a temperature probe in-contact with the multiphase fluid being characterized to allow referencing to data sets or curves fit to the data sets for different temperatures.

Further uncertainty in conducting measurements of crude petroleum oil can be caused by the physical chemistry of the oil, the water, and the mixture itself. For example, in the case of liquid-liquid mixtures undergoing mechanical energy input, the mixture usually contains a dispersed phase and a continuous phase. For water and oil, the mixture exists as either a water-in-oil or an oil-in-water dispersion. When such a dispersion changes from water phase continuous to oil phase continuous, or vice-versa, it is said to "invert the emulsion phase". This is a rheological phenomenon.

A further complicating phase-state phenomena of liquid-liquid mixtures is that stable or semi-stable suspensions of dispersed-phase droplets can sometimes occur. This is usually referred to as an emulsion, which can be either stable or semi-stable. Certain substances are known as emulsifiers and can increase the stability of an emulsion, meaning that it takes a longer time for the emulsion to separate into two phases under the force of gravity or using other means. In the case of petroleum oils, emulsifiers are naturally present in the crude petroleum oil. For example, very stable emulsions can occur during petroleum processing, as either mixtures of water-in-oil or oil-in-water.

For microwave analyzers, whether a dispersion or emulsion is water-continuous or oil-continuous has a significant effect on the analyzer's measurements. In the case of oil-continuous dispersions, the apparatuses and methods of the '060 patent can perform accurate water cut determinations. In the case of water-continuous dispersions or emulsions, the conductivity path established by the water continuous phase causes a significant change in the measured permittivity relative to the same proportion of phases existing as an oil continuous dispersion or emulsion. Additionally, further variations in the conductivity of the aqueous or water continuous phase caused, for example, by even relatively small changes in salinity, can significantly affect the measured permittivity results. Note that when the non-aqueous or oil phase is continuous, no conductivity path is established (because the droplets are not "connected" to form a continuous conducting circuit) and hence there is usually no significant effect on the measurements of a microwave analyzer due to the conductivity of the aqueous phase. Note also that this is only true when the wavelength of the electromagnetic energy is large compared to the emulsion size. When the emulsion size is larger than one eighth of a wavelength, the voltage difference across the emulsion can be significant and therefore a correction must be made with respect to the salinity (conductivity at the frequency of measurement) of the water.

To address the problems of phase inversion uncertainties in aqueous and non-aqueous multiphase mixtures, U.S. Pat. No. 4,996,490 to Scott (the '490 patent), entitled Microwave Apparatus and Method for Measuring Fluid Mixtures and which is hereby incorporated by reference, discloses microwave apparatuses and methods for accommodating phase inversion events. For the example of oil and water mixtures, the '490 patent discloses that whether a particular mixture exists as an oil-in-water or a water-in-oil dispersion can be determined using differences in the reflected and lost microwave power curves in the two different states of the same mixture. The '490 patent discloses microwave apparatuses and methods, including the ability to measure microwave radiation power loss and reflection to detect the state of the dispersion. In further embodiments of that invention, methods are disclosed to compare the measured reflections and losses to reference reflections and losses to determine the state of the mixture as either water-in-oil or oil-in-water, which then allows the proper selection and comparison of reference values relating the measured microwave oscillator frequency to the percentage water. An embodiment of the '490 patent is reproduced from that patent in FIG. 1B, which explained and described in detail later in this application.

However, water cut measurements using the apparatus of the '490 patent can still be subject to uncertainty in the estimation of the total oil output of a given well when the water cuts are very high, such as when they are over 90%, and approaching 100%. To illustrate, consider the uncertainty associated with measuring the water cut of a 99% water cut oil using electromagnetic characterization using a microwave analyzer. Assume that the electromagnetic characterization stage has a frequency measurement uncertainty of 1000 Hz, or 0.001 MHz. Further assume that a 3.72% shift in actual water cut percent units, or oil cut percent units, results in a 1 MHz change in frequency of the electromagnetic characterization. Thus, the resulting uncertainty band is 0.00372% wide in water cut percentage units. If this uncertainty band is applied to a 99% water cut oil, then the 1% oil cut value has an uncertainty of 0.372% (e.g. 0.00372 uncertainty span divided by 1, times 100 to convert to percent value, equals 0.372% uncertainty). If the measurement of the 1% water cut has an uncertainty of 0.372% and the oil well has an output of 100 barrels per day, the uncertainty in total production over five years is almost 680 barrels of oil.

Thus, solving the problem of accurately ascertaining the output of crude petroleum from a high water cut well presents challenges and requires solutions not adequately met by current approaches. More particularly, there is an increasing need for reduction of uncertainty in the measurement of crude oil as the value of petroleum continues to rise. More specifically, as the use and development of different production enhancement techniques continues to increase, the dynamics of compositional fluctuations at the wellhead adds further challenges to accurately determining crude petroleum oil production output.

The present application discloses systems and methods for determining the amount of water in a multiphase flow stream. A multiphase flow stream is subjected to a separation process to produce an oil-enriched fractional stream. Measurements of water content can then be made with reduced uncertainties. The amount of water in the original multiphase flow stream can be determined using the measured water content of the oil-enriched fractional stream and the flow rate of at least one of the streams through the separator.

In some embodiments (but not necessarily all), the disclosed innovations can be used at the wellhead of (or slightly downstream from) a producing hydrocarbon well, to estimate its oil, water, and gas output.

In some embodiments (but not necessarily all), the disclosed ideas can be used to estimate the water phase fraction and the oil phase fraction in a multiphase flow stream which is subjected to a single or to multiple hydro-cyclone separations.

In some embodiments (but not necessarily all), the disclosed ideas can be used to estimate the water phase fraction and the oil phase fraction in a saline water-continuous crude petroleum oil flow stream from which enough water has been removed to invert the flow stream to oil-continuous.

The disclosed innovations, in various embodiments, provide one or more of at least the following advantages:

Some of the disclosed innovations can provide methods and systems to improve the measurement of high water cut hydrocarbon well production output using a single measurement system with improved accuracy across a wide variety of operating conditions.

Some of the disclosed inventions provide more accurate physical or electrical property measurements in an oil and water mixture flow stream.

Some of the disclosed inventions reduce the number of measurements required to determine the amount of water in an oil and water mixture flow stream.

Some of the disclosed inventions provide near-real-time reduction of errors and supply more accurate results to aid in near-real-time decision-making, without requiring multiphase fluid flow stream sampling or off-line labwork conducted on such samples and thus eliminating the cost, lost opportunities, and hazards associated with such sampling.

BRIEF DESCRIPTION OF THE DRAWINGS

The disclosed inventions will be described with reference to the accompanying drawings, which show important sample embodiments of the invention and which are incorporated in the specification hereof by reference.

FIG. 1C shows a table of flow balances for hydro-separators, wherein the hydro-separators are hydro-cyclones.

DETAILED DESCRIPTION OF THE PREFERRED EMBODIMENTS

The numerous innovative teachings of the present application will be described with particular reference to a presently preferred embodiment (by way of example, and not of limitation).

Figure 1:
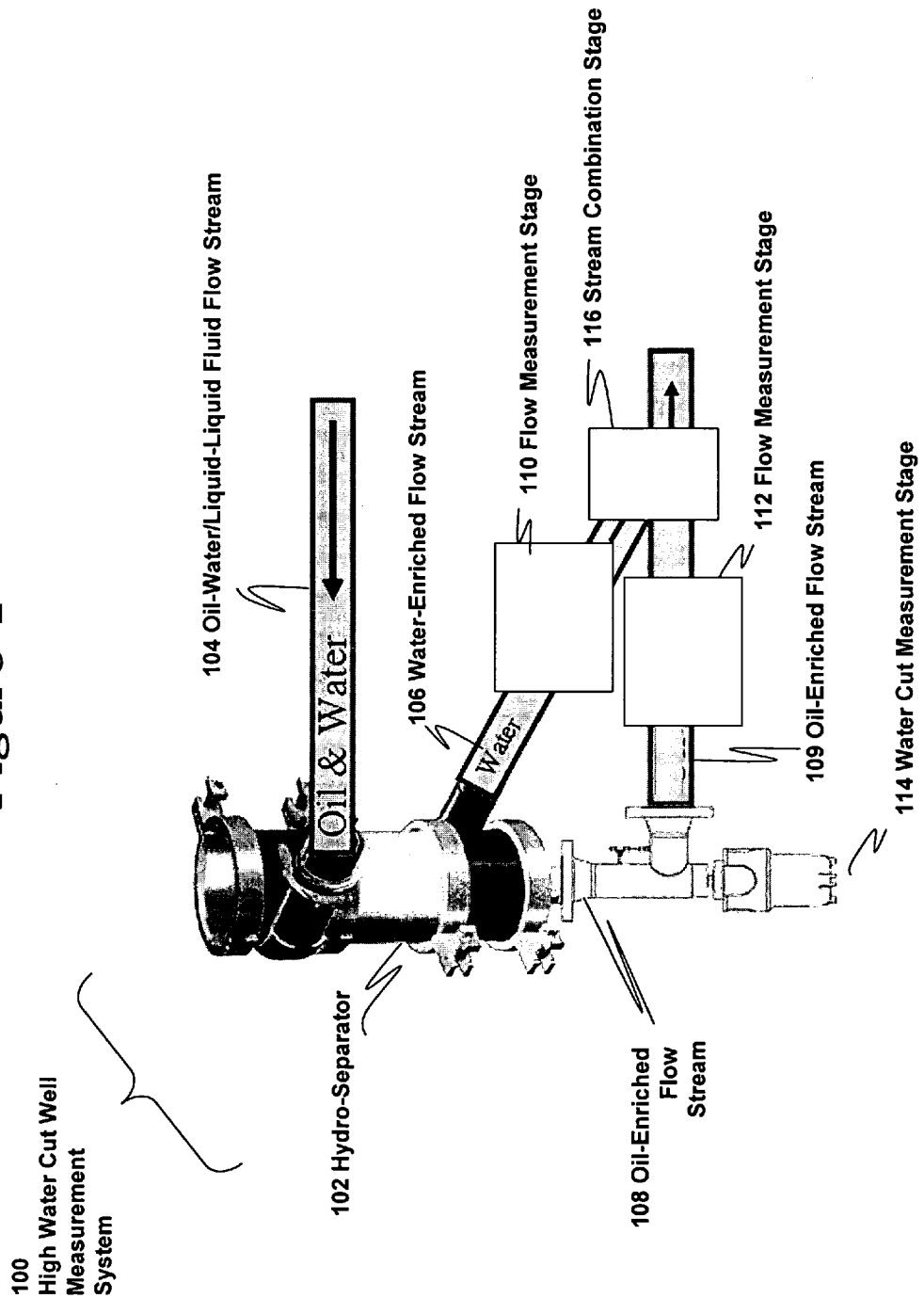
FIG. 1 shows a high water cut well measurement system using a hydro-separator, consistent with various embodiments of the present application.

FIG. 1 shows one embodiment of a high water cut well measurement system 100 consistent with the present application. An oil-water liquid-liquid fluid flow stream 104, which can be a water-continuous dispersion with a water cut of about 80% or higher, can enter hydro-separator 102.

Hydro-separator 102 can be, in a preferred embodiment, a liquid-liquid hydro-cyclone, which is a type of separator known to a person having ordinary skill in the art of petroleum and oil field equipment design, selection, and operation, as shown in FIG. 1. Hydro-cyclones can separate oil from an oil and water mixture, or, viewed in the alternative, water from an oil and water mixture. Hydro-cyclones are described in Chapter 15 of the Petroleum Engineering Handbook, which is hereby incorporated by reference. In one embodiment of the present application, a hydro-cyclone as hydro-separator 102 can receive an oil and water mixture flow stream 104, essentially free of gas, which can enter tangentially into the hydro-cyclone. The kinetic energy supplied by the flow stream as its pressure is reduced contributes to causing the multiphase fluid within the hydro-cyclone to spin, at forces as high as hundreds or thousands of times the force of Earth's gravity. The water phase, being the heavier phase, is generally forced against the hydro-cyclone wall and then can exit the hydro-cyclone as stream 106. Stream 106 can pass through flow measurement stage 110.

A water-enriched phase flow stream can thus be separated from stream 104 as stream 106. If the hydro-cyclone is designed to produce an essentially pure water stream as stream 106, the concentration of oil in the water can be a negligible amount, in the magnitude of parts per million oil in water by volume, as readily known to one skilled in the art of oil and water separations using hydro-cyclones.

The oil, being lighter in density than the water, is forced to the center of the hydro-cyclone and can flow out in oil-enriched discharge flow stream 108. The hydro-cyclone can thus subject the oil and water mixture to centripetal or centrifugal force, thereby effecting the separation, or oil-enriching action.

FIG. 1C shows a table of different examples of flow balance calculations for a hydro-separator as embodied by a hydro-cyclone. For the purpose of clarity for the description of the flow balances of hydro-separator systems which can utilize some or all of the present innovations, but not as a limitation of the present application, FIG. 1C will be described with reference to the system of FIG. 1. The table of FIG. 1C contains calculations for a "two inch" and a "three inch" hydro-cyclone, where the two and three inch dimension generally refers to the outer diameter of the hydro-cyclone. Note also that the wall thicknesses of the hydro-cyclones are considered negligible for the illustrative purpose of the table. Column A shows a range of water cuts from 80% to 98% for stream 104. Column B shows an assumed total volumetric flow rate of 200 cubic meters per day for all flow balance Examples 1 through 11. Column C shows the actual daily volume of water flow stream 104 for the different water cuts, calculated by multiplying A times B. Column D shows the actual daily volume of oil for the different water cuts, calculated by multiplying (1 minus A) times B. Column E shows the inner diameter of the hydro-cyclone circular internal partition, assumed as one inch, or 0.0254 meters, for both the "two inch" and the "three inch" hydro-cyclone. Column F shows the outer circular diameter as 0.0508 meters for the "two inch" hydro-cyclone and 0.0762 meters for the "three inch" hydro-cyclone. Column G shows a calculation of the annular cross sectional area formed between the inner and outer circular diameters. Column H shows the cross section area of the inner circular internal partition as 0.00051 square meters for all examples, since the inner diameter was assumed to remain constant. Column I shows the total cross sectional area of the hydro-cyclone examples. Column L shows the daily volume of flow of hydro-separated stream 106, which can be pure water, which is separated by the previously-described centripetal or centrifugal action where the more dense water phase is forced against the outer wall of the hydro-cyclone, and which is calculated by multiplying the fraction of the total cross sectional area occupied by the annulus (Column G divided by Column I) times Column B, where the fractional flow through the annulus is assumed to be proportional to the fractional area of the annulus. Column M shows the daily volume of flow of enriched oil phase stream 108, calculated by subtracting Column L from Column B. Column N shows the reduced water cut for the enriched oil phase produced as stream 108, calculated by subtracting Column D from Column M, and then dividing the difference by Column N, and then multiplying times 100 to obtain percent water cut.

Referring again to FIG. 1, oil-enriched stream 108 can pass through water cut measurement stage 114. Contained in stream 108 can be essentially 100% of the oil in stream 104. Oil-enriched stream 109 discharges from stage 114 and can be measured for flow rate in flow measurement stage 112.

Figure 1A:
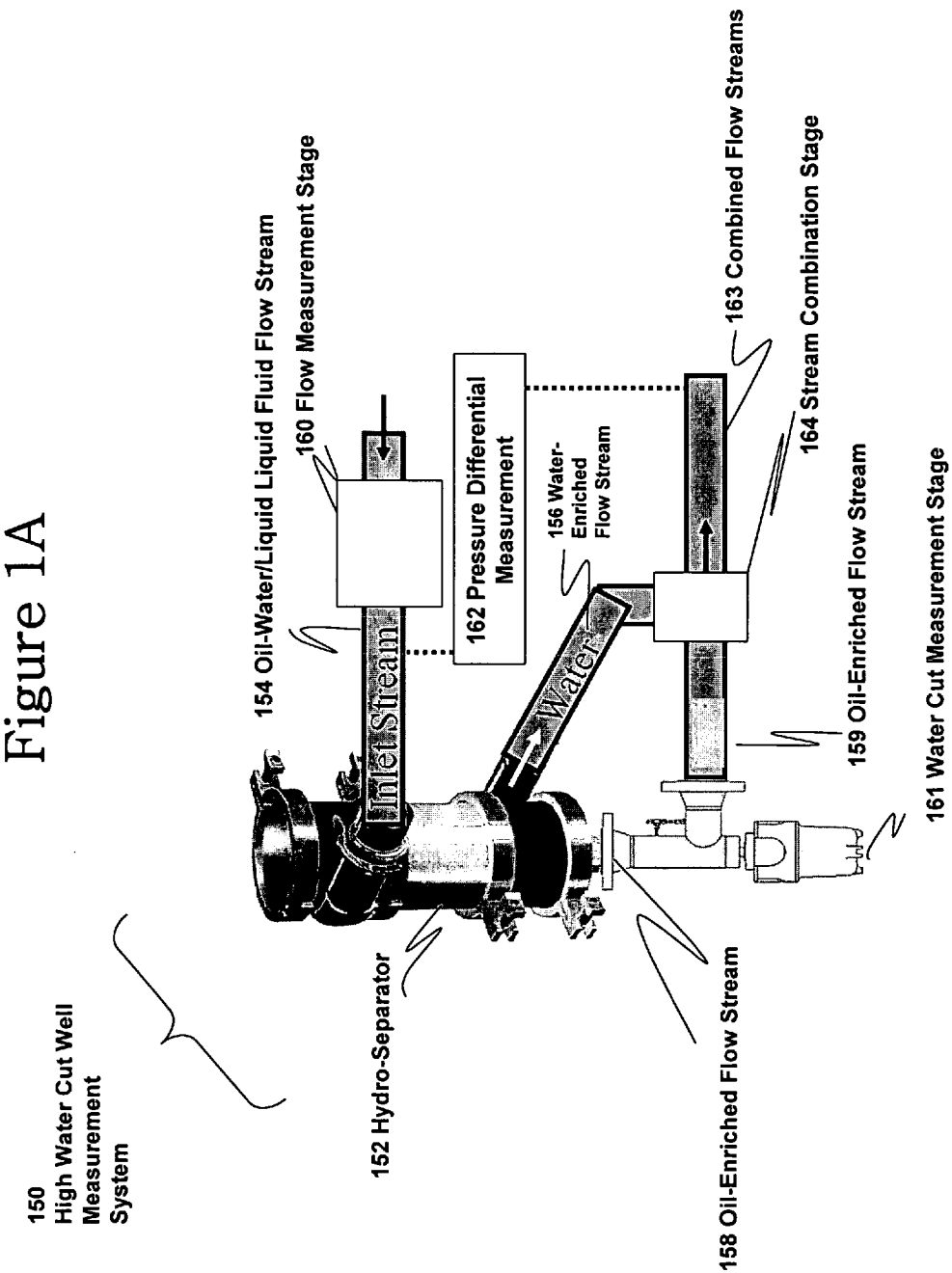
FIG. 1A shows a high water cut well measurement system using a hydro-separator, consistent with various embodiments of the present application.
Figure 1B:
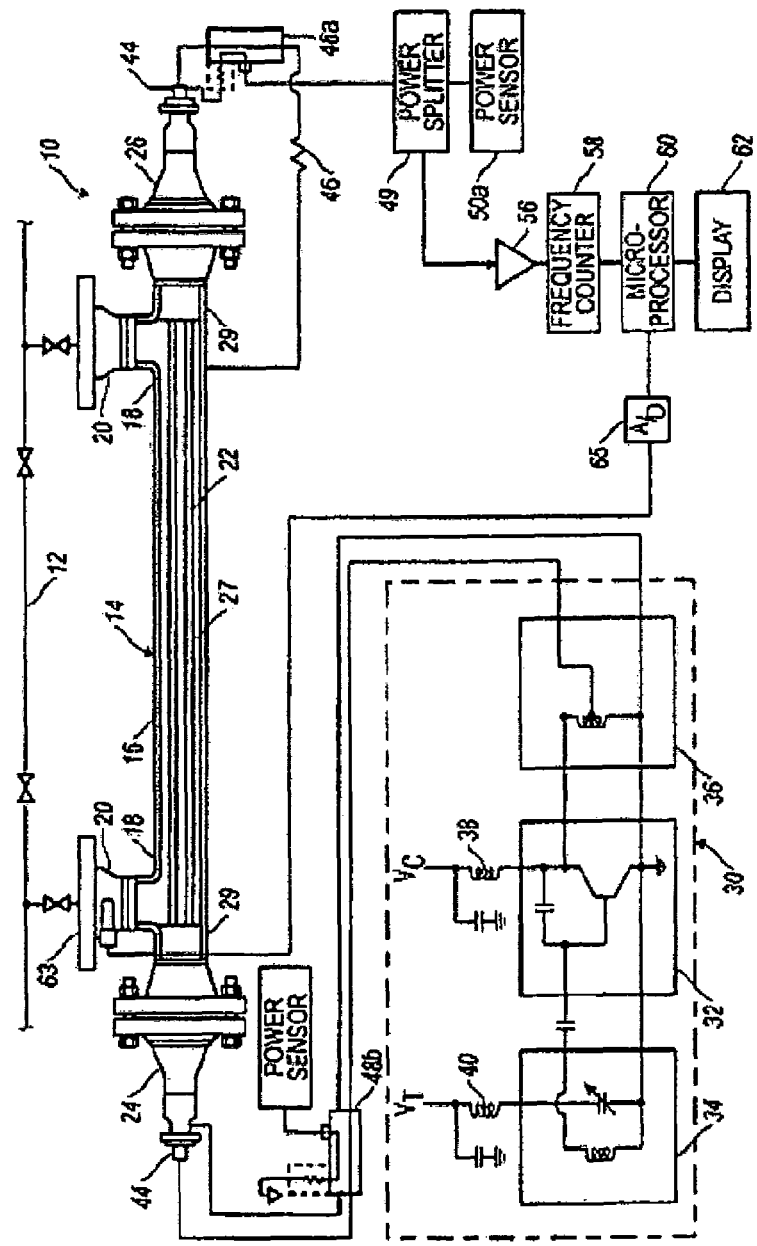
FIG. 1B shows a reproduction of an embodiment of U.S. Pat. No. 4,996,490 as an example of an electromagnetic characterization apparatus, consistent with various embodiments of the present application.

One embodiment of stage 114 is shown in FIG. 1B. In a preferred embodiment, a microwave analyzer can perform the function of water cut measurement in stage 114.

In another embodiment, a densitometer can perform the function of stage 114 by performing a water cut by density determination. In one embodiment, the densitometer can be a Coriolis meter.

Streams 106 and 108 can be combined in stream-combining stage 116.

A preferred embodiment of stage 110 or stage 112 is a turbine meter. Another embodiment of stage 110 or stage 112 is a Coriolis meter.

Another embodiment is to combine the functions of water cut by density measurement, as can be performed in stage 114, and flow rate measurement as can be performed in stage 112, by using a Coriolis meter.

It has been found that because about 40-100% of the water can be removed from a stream, a significant reduction in the uncertainty of the produced oil from the well can be achieved.

For example, consider the reduction in uncertainty when using hydro-separation and the systems and/or methods of the present application in which the water cut is determined using electromagnetic characterization as stage 114. For example, assume that stream 104 has a true oil cut of 1% and that it is flowing at 1000 kilograms per hour (kg/hr). Thus, stream 104 composition consists of 990 kilograms of water and 10 kilograms of oil. Assume that hydro-separator 102 separates 900 kilograms of a water-enriched fraction as stream 106 from stream 104 during a one hour period, where the concentration of oil in stream 106 has been reduced to a negligible amount of 100 ppm. In that case, stream 108 has an average flow rate of 100 kilograms per hour and consists of 10 kilograms of oil and 90 kilograms of water, with a resulting oil cut of nominally 10%. Assume that the oil cut of stream 108 is being measured with an electromagnetic characterization stage at water cut measurement stage 114. Assume that the electromagnetic characterization stage has a frequency measurement uncertainty of 1000 Hz, or 0.001 MHz. Assume that the errors associated with flow measurement stages 110 and 112 are negligible. Further, assume that a true 3.72% shift in actual water cut percent units, or oil cut percent units, results in a 1 MHz change in frequency of the electromagnetic characterization. Thus, the resulting uncertainty band is 0.00372% wide in oil or water cut percentage units. If the systems and/or methods of the present application are not applied, the uncertainty in the amount of oil production is 0.372%, where the percentage uncertainty for the 1% oil cut value is calculated by dividing 0.00372% by 1%, and multiplying times 100 to convert to percentage uncertainty. If the methods and systems of the present application are applied, and an oil cut of 10% results because the hydro-separator removes 900 kilograms of water as previously described in this example, then the 10% oil cut value has a resulting uncertainty of 0.0372%, where the percentage uncertainty for the 10% oil cut value is calculated by dividing 0.00372% by 10%, and multiplying times 100 to convert to percentage uncertainty. This represents a ten-fold reduction in uncertainty associated with the water cut determination stage.

For a further example, consider the reduction in uncertainty when using hydro-separation and the systems and/or methods of the present application in which the water cut is determined using densitometry as stage 114. For example, assume that stream 104 has a true oil cut of 1% (99% water cut) and that it is flowing at 1000 kilograms per hour (kg/hr). Thus, stream 104 composition consists of 990 kilograms of water and 10 kilograms of oil. Assume that hydro-separator 102 separates 900 kilograms of a water-enriched fraction as stream 106 from stream 104 during a one hour period, where the concentration of oil in stream 106 has been reduced to a negligible amount of 100 ppm. In that case, stream 108 has an average flow rate of 100 kilograms per hour and consists of 10 kilograms of pure oil and 90 kilograms of water, with a resulting oil cut of 10% (90% water cut). Assume that the oil cut of stream 108 is being measured with a densitometer. Assume that the true density of the oil phase is 950 kg/m3 and the true density of the water phase is 1050 kg/m$^3$. At 10% oil cut, the density of the mixture is therefore 1040 kg/m$^3$. Assume that the densitometer has a measurement uncertainty of 0.2%. When this uncertainty percentage is applied to the mixture density of 1040 kg/m$^3$, the resulting uncertainty is 2.08 kg/m$^3$, where the uncertainty is calculated by multiplying 0.002 times 1040 kg/m$^3$. Because the span between pure oil and pure water phase is 100 kg/m$^3$ for the particular assumed densities of oil and water, this represents an uncertainty of about 2.1% in water cut or oil cut percentage units. With the benefit of the hydro-cyclone and the systems and/or methods of the present innovations, the densitometer is able to establish definitively that the well is producing oil, and to estimate the production with an uncertainty of 1.9% percentage units associated with the determined oil cut value of 10%. Thus, the uncertainty in the value for the amount of oil produced will be 19%. Without the benefit of the hydro-cyclone and the systems and/or methods of the present innovations, the uncertainty is 100% because the densitometer is incapable of distinguishing a 1% from a pure water phase, given the assumed operating parameters as previously described.

FIG. 1A shows another embodiment of a well measurement system 150 consistent with the present application, which requires only one flow meter, rather than two, as compared to FIG. 1. An oil-water liquid-liquid flow stream 154, which can be a water-continuous dispersion with a water cut of about 80% or higher, can pass through flow measurement stage 160 and enter hydro-separator 152.

Hydro-separator 152 can be, in a preferred embodiment, a liquid-liquid hydro-cyclone, as described previously. In one embodiment of the present application, a hydro-cyclone as hydro-separator 152 can receive an oil and water mixture flow stream 154 essentially free of gas, which can enter tangentially into the hydro-cyclone and be processed by it as previously described. The water-enriched fraction can exit the hydro-separator as stream 156. The oil-enriched phase can flow out as discharge flow stream 158 and pass through water cut measurement stage 161. Flow stream 156 and 158 can be combined in stream combination stage 164. The differential pressure between stream 154 and stream 163 can be measured by pressure differential measurement stage 162. As known by one skilled in the art of hydro-cyclone operations, the flow rates of streams 156 and 158 can be determined if one knows the flow rate into the hydro-separator 152, as can be determined by stage 160, and the differential pressure drop across the hydro-separator as can be determined by stage 162. Thus, only one flow meter is required in system 150.

Microwave analyzers can perform the function of water cut electromagnetic measurements in water cut measurement stage 161. U.S. Pat. No. 4,996,490 describes some of the preferred embodiments of microwave analyzers to be used in the present application.

In another embodiment, a densitometer can perform the function of stage 161 by performing a water cut by density determination. In one embodiment, the densitometer can be a Coriolis meter.

FIG. 1B shows illustrated a diagram of an apparatus for measuring the concentration of one substance or material such as water, in another substance or material such as crude petroleum oil, which is being transmitted as a liquid mixture flow stream through a pipeline. The apparatus is generally designated by the numeral 10 and is particularly adapted for interconnection with a fluid transmission pipeline 12 for sampling the pipeline flow stream. Alternatively, the apparatus 10 might become part of the pipeline. The apparatus 10 includes a fluid flow conducting and measurement section 14 comprising an outer conduit section 16, including spaced apart pipe tee sections 18 having conventional flange portions 20 formed thereon for connection to branch conduit portions of the pipeline 12. The measurement 14 comprises a coaxial transmission line which includes a center conductor 22 preferably formed of a metal such as stainless steel which extends between opposed end support parts 24 and 26 which are described in detail in the above-referenced patent application. The center conductor 22 preferably comprises a generally cylindrical rod or tube member coaxially arranged in the conduit 16 and provided with an outer sheath 27 formed of a material having a relatively low dielectric loss tangent, preferably less than 0.1 at a frequency of 1.0 GHz. The sheath 27 preferably comprises a relatively easy-to-fabricate plastic such as polypropylene, a plastic sold under the trademark DELRIN or one of the fluorocarbon plastics. Alternatively, certain ceramics or other materials may also be used as the outer sheath 27 as long as they are low loss tangent dielectric materials. The fit between the outer sheath 27 and the center conductor 22 is preferably a forced or line-to-line fit although some clearance may be permitted as long as fluid flow between the center conductor and the outer sheath is prohibited. In an apparatus where the center conductor has a diameter of 0.25 inches, the outer diameter of the sheath 27 is preferably at least about 0.50 inches or, alternatively, a ratio of the outer diameter of the sheath to the outer diameter of the center conductor is in the range of about two to one.

It has been determined that with the provision of a sheath 27 formed of one of the above-mentioned materials and in the proportions described, that the electrical circuit for propagating microwave radiation through the apparatus 22 retains a high quality signal resolution characteristic in liquid mixtures of oil and water, for example, wherein the water content is relatively high, that is on the order of more than 5% to 10% by volume. With this type of center conductor arrangement, the circuit associated with the apparatus 10 and described herein below retains good field intensity or prevents short circuiting of the center conductor to the outer conductor in an unwanted location, the oscillator circuit retains its good load-pulling characteristics with good resolution of phase and the interface between the sheath 27 and the fluid in the conduit 16 is a new propagation medium which has desirable operating characteristics.

When the apparatus 10 is operating with a liquid composition which is high in water content or a so-called water continuous phase, the conductivity of the composition is high compared to a good dielectric but low compared to a good conductor and, of course, the liquid composition is in direct contact with the wall surfaces of the measurement section 14 including the center conductor. The insulating sheath 27 prevents the radio frequency (RF) energy from being shorted out immediately at the point where the RF energy enters the measurement section or where the fluid cross section begins. Moreover, the sheath 27 now becomes the primary region where the RF field is propagated with the conductive fluid becoming a pseudo outer wall of the measurement section in place of the wall of the conduit 16. The cross sectional measurement of the water-in-oil composition is still preserved due to the large skin depth of the microwave or RF energy at the operating frequency. This skin depth is large through the water as the conducting medium of the outer half of the coaxial transmission line formed by the measurement section. The dielectric structure is now the sheath 27. The properties of the propagated RF energy still reflect the changing content of the oil in the water and this is related through pulling of the unisolated oscillator which is described herein below. The sheath 27 must be thick enough to maintain a reasonable coaxial impedance to be able to propagate the RF energy into the measurement section 14 and maintain a measurement capability. A very thin dielectric coating on the center conductor 22 will cause a very low impedance with a liquid composition having a high water content and therefore the RF energy would be reflected at the fluid interface.

RF energy is not propagated in the interior of a good conductor. The conductor guides the electromagnetic waves. The energy travels in the region between the conductors in a coaxial transmission system with a good dielectric. The currents that are established at the conductor surfaces propagate into the conductor in a direction perpendicular to the direction of the current density. The current density or electric field intensity established at the surface of a good conductor decays rapidly looking into the conductor. When the conductor is resistive or, low conductivity, this depth into the conductor increases rapidly. This phenomenon is known in the art as skin depth.

As shown in FIG. 1B, the center conductor 22 extends through opposed end block members 29 which are also preferably formed of a relatively high insulative material such as a fluorocarbon plastic and the end plug sections are configured in a way similar to the ones described in the above-referenced patent application.

The measurement section 14 is operably connected to a source of radio frequency (RF) or so-called microwave energy comprising an unbuffered or unisolated, free-running oscillator, generally designated by the numeral 30. The oscillator 30 includes an active circuit 32 operably connected to a tuning circuit 34 and to an impedance matching network circuit 36. The circuit 32 is adapted to receive a constant DC voltage, Vc, from a source not shown and by way of a filter circuit 38. The tuning circuit 34 is also adapted to receive a controllable DC voltage, Vt, from another source, not shown, by way of a second filter circuit 40. The oscillator 30 has an appreciable load-pulling characteristic. The fundamental operating frequency of the oscillator is changed as the complex load is changed on the output circuit of the oscillator. The oscillator 30 is preferably of a type commercially available such as from Avantek Company, Santa Clara, Calif. as their model VTO 8030 voltage controlled oscillator. The exemplary oscillator 30 has a maximum load-pulling characteristic of about 35 MHz at a nominal 200 MHz operating frequency into all phases of a short circuit at the end of a 50 Ohm line stretcher (approximately 0.5 dB return loss). The oscillator 30 is operably connected to the apparatus measurement section 14 through a suitable connector 44 which is in electrically conductive engagement with the center conductor 22 at the end part 24 and at the opposite end of the center conductor 22 through a second connector 44, a resistance 46 and with the outer conductor or conduit 16 as illustrated. The end part 26 is also adapted to connect the center conductor 22 with a 10 dB directional coupler 48a which is operable to sample the microwave energy or power transmitted through the coaxial measurement section 14. The coupler 48a is connected to a power splitter 49 which is connected to a power sensor 50a. The directional coupler 48a may be of a type manufactured by Minicircuits Company of Brooklyn, N.Y. as their model ZED-15-2B. The power splitter 49 may be of a type ZFSC-2-2 also manufactured by Minicircuits. The power sensor 50a may be of a type 437B manufactured by Hewlett Packard of Sunnyvale, Calif.

A second directional coupler 48b is interposed in the circuit between the end part 24 and the oscillator 30 and is connected to a second power sensor. The directional couplers 48a and 48b may be of identical configuration. The coupler 48a is connected to the power splitter 49 which provides an output signal which is amplified by an amplifier 56. The output of the amplifier 56 is adapted to be input to a frequency counter 58 which is also adapted to be connected to a microprocessor 60. A suitable digital display or readout device 62 is connected to the microprocessor 60. The amplifier 56 may be of a type commercially available from the above-mentioned Minicircuits Company as their model ZFL-500. The frequency counter 58 may be of a type manufactured by Hewlett Packard Company as their model 5342A and the microprocessor 60 may be a Hewlett Packard type 9836. The system illustrated in FIG. 1B preferably includes a temperature compensation circuit including a thermocouple 63 operably connected to a conversion circuit 65 to provide a suitable digital signal to the microprocessor 60.

In operation, the changing dielectric constant presented by the material flowing through the measurement section 14, such as caused by the presence in a liquid mixture, for example, of varying amounts of water in oil or oil in water, causes the oscillator 30 to change its operating frequency over a relatively narrow frequency band as compared with the nominal operating frequency of the oscillator. For example, the oscillator 30, in a preferred form, can be pulled from its nominal operating frequency through a range of about 20 MHz by the changing dielectric constant of the medium flowing through the measurement section 14.

Figure 2:
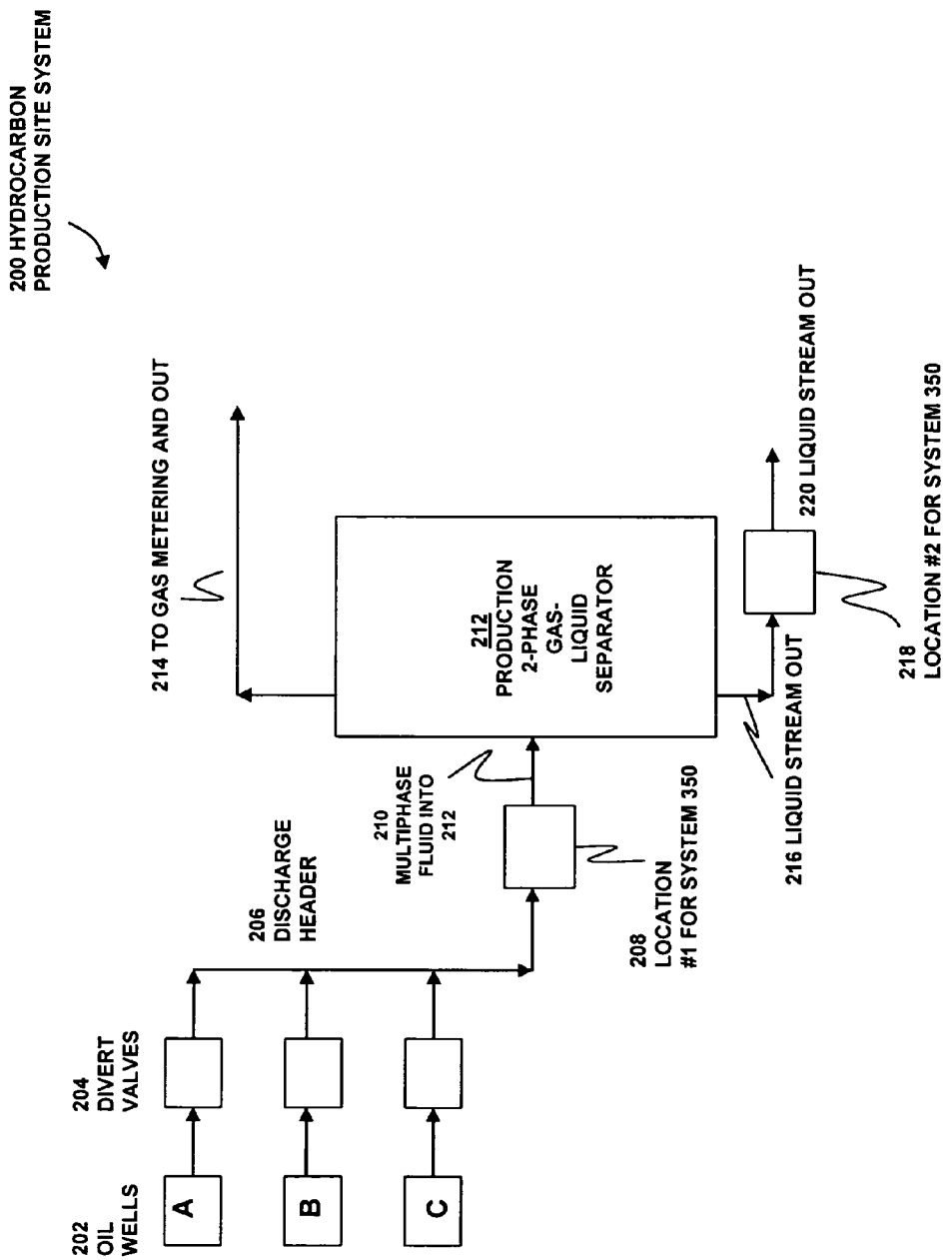
FIG. 2 shows a hydrocarbon production site employing a two-phase production gas-liquid separator, consistent with various embodiments of the present application.

FIG. 2 shows one embodiment of a hydrocarbon production site system 200 consistent with the disclosed innovations for measuring the water cut of a high water cut crude petroleum oil stream using hydro-separation. The site system of FIG. 2 can be used, in some embodiments, with the systems embodied in FIG. 1, FIG. 1A, and/or FIG. 3, and/or the method embodied in FIG. 4. For the purpose of clarity for the description of one embodiment of the site systems which can utilize some or all of the present innovations, but not as a limitation of the present application, the site system of FIG. 2 will be described with reference to the system of FIG. 3.

Multiple oil production wells 202 can produce crude oil flow streams which can be individually diverted to be characterized by using diversion valves 204 discharging through discharge header 206. High water cut well measurement system 350 can be installed in at least two locations in production site 200, as locations 208 and 218.

In one embodiment in location 208, system 350 can characterize the total flow in discharge header 206 from a selected well, including the amounts of gases, water, and petroleum crude oil. Stream 210 can exit the measurement system from location 208 and can enter the production gas-liquid separator system 212, if one or more such separators are present on site 200. If so, the gases can exit production separator 212 as stream 214 and can be collected, further processed, metered, and/or transported. Liquids can exit production separator as stream 216.

In another embodiment, at location 218, system 350 can measure the exiting liquid stream 216 of production gas-liquid separator 212, if one or more are present on site 200. If so, in this location, system 350 may not need gas-liquid separator 360 and the associated gas processing components 364, and 366, if separator 212 is performing to an efficiency that removes essentially all of the gas from stream 210.

Note that even if located in location 218, system 350 may retain separator 360 to insure that any remaining gas can be properly accounted for as well as be essentially fully removed from the liquid-liquid stream 216 to be then measured for water cut in stage 390. If system 350 is located at location 218, stream 220 can exit system 350 and be further processed or transported.

Figure 2A:
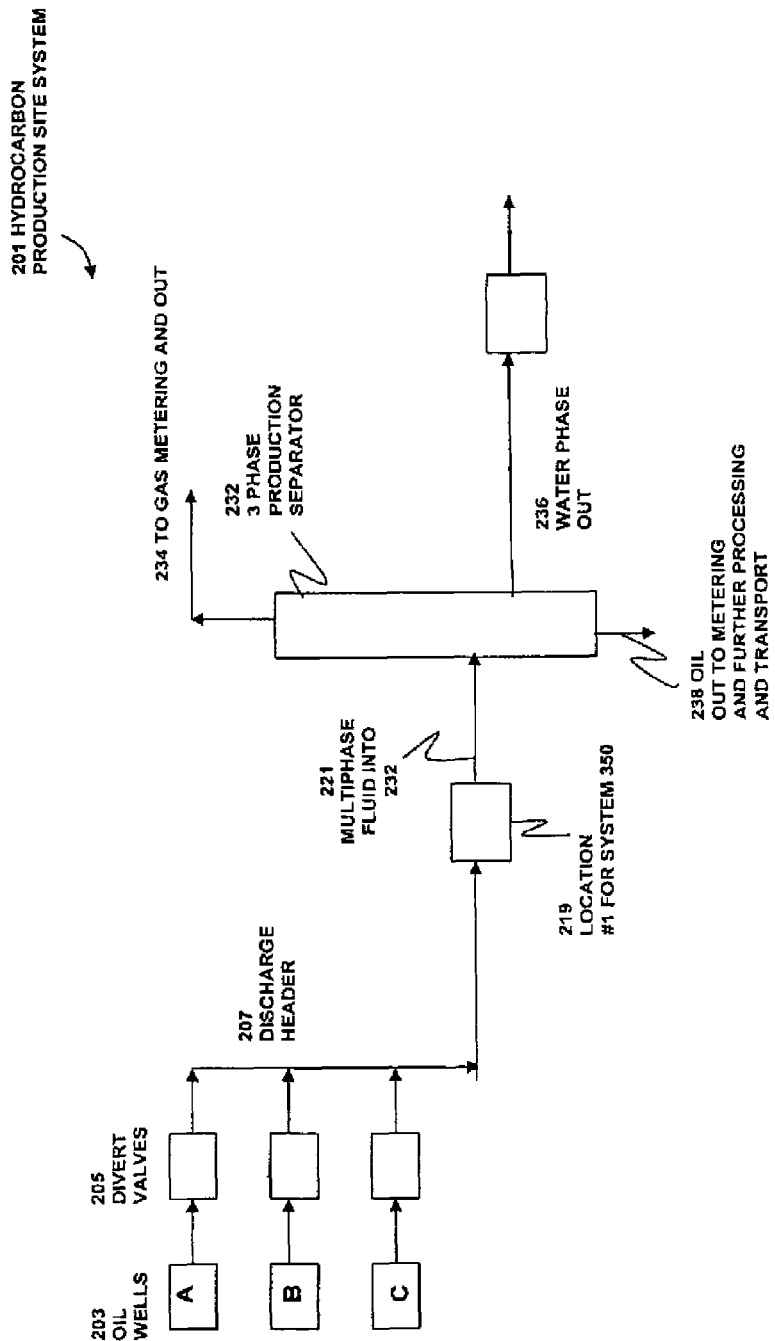
FIG. 2A shows a hydrocarbon production site employing a three-phase production gas-liquid-liquid separator, consistent with an embodiment of the present application.

FIG. 2A shows another embodiment of a hydrocarbon production site system 201 wherein an alternative separator mode employs a production three phase separator system 232. Discharging from wells 203 is discharge header 207. A first possible location for system 350 in FIG. 2A is location 219 which receives a multiphase fluid flow stream from discharge header 207. Stream 221 can then exit system 350 and can enter separator 232. Exiting separator 232 is gas fraction flow stream 234, less dense liquid fraction oil-enriched flow stream 238, and more dense liquid fraction flow stream, e.g. water, or aqueous stream 236. If separator 232 malfunctions, or is designed improperly, and is not able to remove all of the oil from the water phase in stream 221, then flow stream 236 can be monitored by system 350 (or the system of FIG. 1 or the system of FIG. 1A) consistent with the present application.

Gas-liquid production separators are described in Chapter 12 of the third printing of the Petroleum Engineering Handbook, which is hereby incorporated by reference. FIGS. 12.23 and 12.25 from the Handbook show schematics of typical production gas-liquid separators as can be used as production separator 212. Additionally, FIGS. 12.29 through 12.31 show various metering applications that can be applied to such separators. FIG. 12.20 shows a three phase production separator which can be used as production separator 232.

Figure 3:
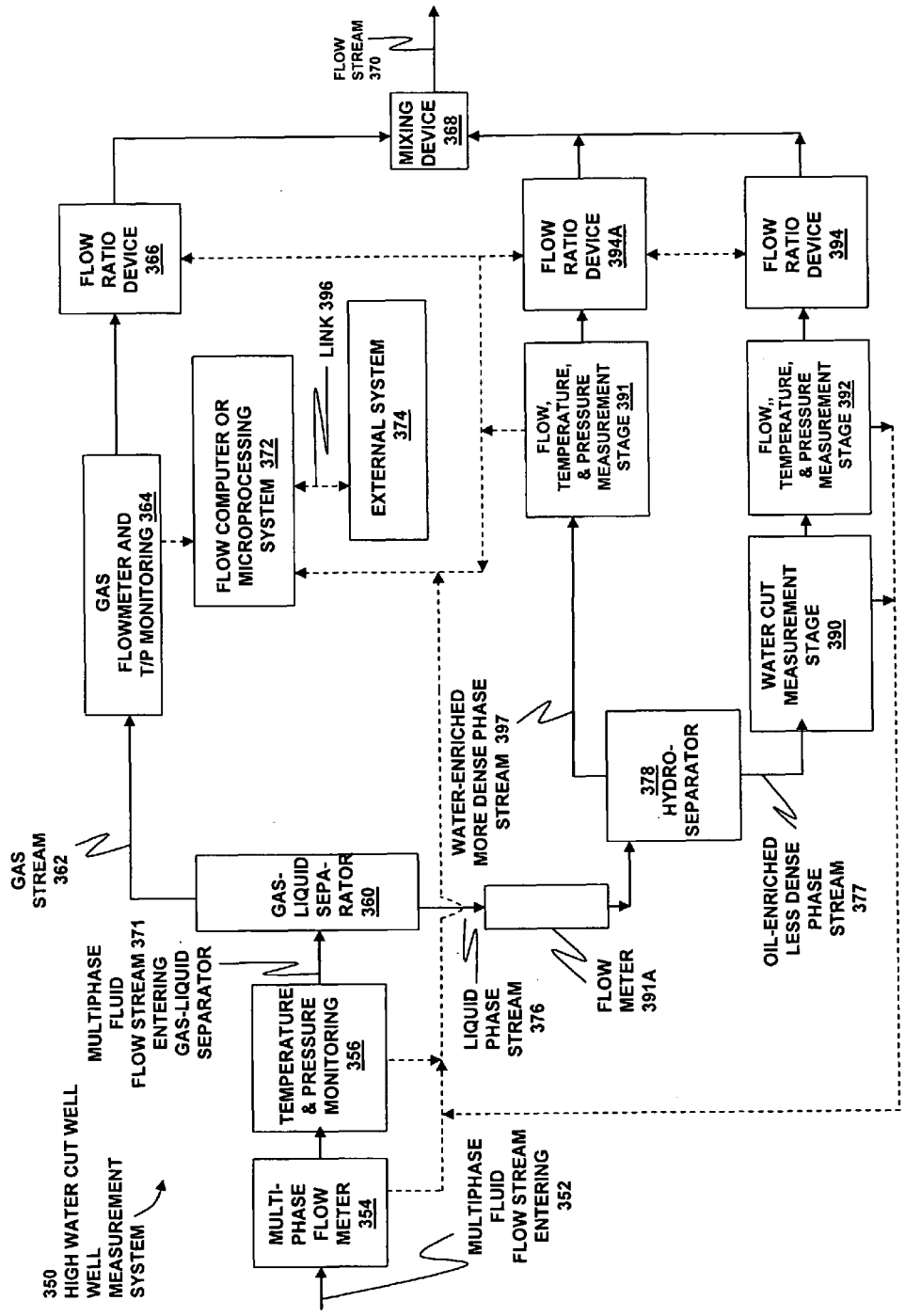
FIG. 3 shows a high water cut well measurement system, consistent with various embodiments of the present application.

FIG. 3 shows a preferred embodiment of a high water cut well measurement system 350 consistent with the present application. In FIG. 3, an oil-water multiphase fluid flow stream 352, which can be a water-continuous dispersion with a water cut of about 80% or higher, can enter the well measurement system 350.

In one embodiment, stream 352 can be metered for flowrate by flow meter 354. In one embodiment, flow meter 354 can be a turbine meter. In another embodiment, flow meter 354 can be a Coriolis meter. In one embodiment, the temperature and pressure of stream 352 can be monitored for temperature and pressure by device or devices 356. In one embodiment, flow stream 371 can enter gas liquid separator 360. In one embodiment, the gas fraction flow stream 362 exits separator 360 and the flow rate, temperature, and/or pressure can be monitored at 364. In one embodiment, a flow ratio function can be performed to maintain the flow ratio of flow stream 362 by a suitable device at 366 in concert with devices 394 and 394A, as indicated by the dashed signal connections between devices 366, 394A, and 394, and flow computer 372.

A liquid-liquid multiphase flow stream 376 can exit separator 360 and can be can be metered for flow by flow meter 391A. Flow meter 391A is analogous to flow meter 160 in FIG. 1A. Stream 376 can enter hydro-separator 378 where stream 376 can be split into two streams. Note that hydro-separator 378 is analogous to separator 102 in FIG. 1 and 152 in FIG. 1A. Discharging from hydro-separator 378 is a less-dense liquid flow stream 377, enriched with the less dense of the two liquids, such as being oil-enriched. Also discharging from hydro-separator 378 is more dense fraction liquid flow stream 397, enriched with the more dense of the two liquids, such as being water-enriched. The degree of enrichment of the respective streams can be determined by the composition and physical properties of the liquid-liquid mixture and its components, as well as the design and operating parameters of hydro-separator 378 as known to a person having ordinary skill in the design and operations of oil-water hydro-cyclone separators.

Less dense liquid, e.g. oil-enriched phase flow stream 377 can be measured for water cut at stage 390 and can be monitored for flow rate, and temperature, and pressure at stage 392. U.S. Pat. No. 4,996,490 describes some of the preferred embodiments of water cut electromagnetic characterization analyzers to be used in the present application in the water cut measurement stage 390.

In one embodiment, stage 390 can be a densitometer that determines water cut by the density method.

The flow ratio of stream 377 can be maintained relative to streams 397 and 362 by a suitable device at 394 acting in concert with devices 394A and 366.

The more dense fraction liquid, e.g. flow stream 397 can be monitored for flow rate at stage 391. The flow ratio of stream 397 can be maintained on stream 397 relative to streams 362 and 377 by a suitable device at 394A.

Streams 362, 377, and 397 can be combined in mixing device 368 and then exit system 350 as stream 370.

Figure 4:
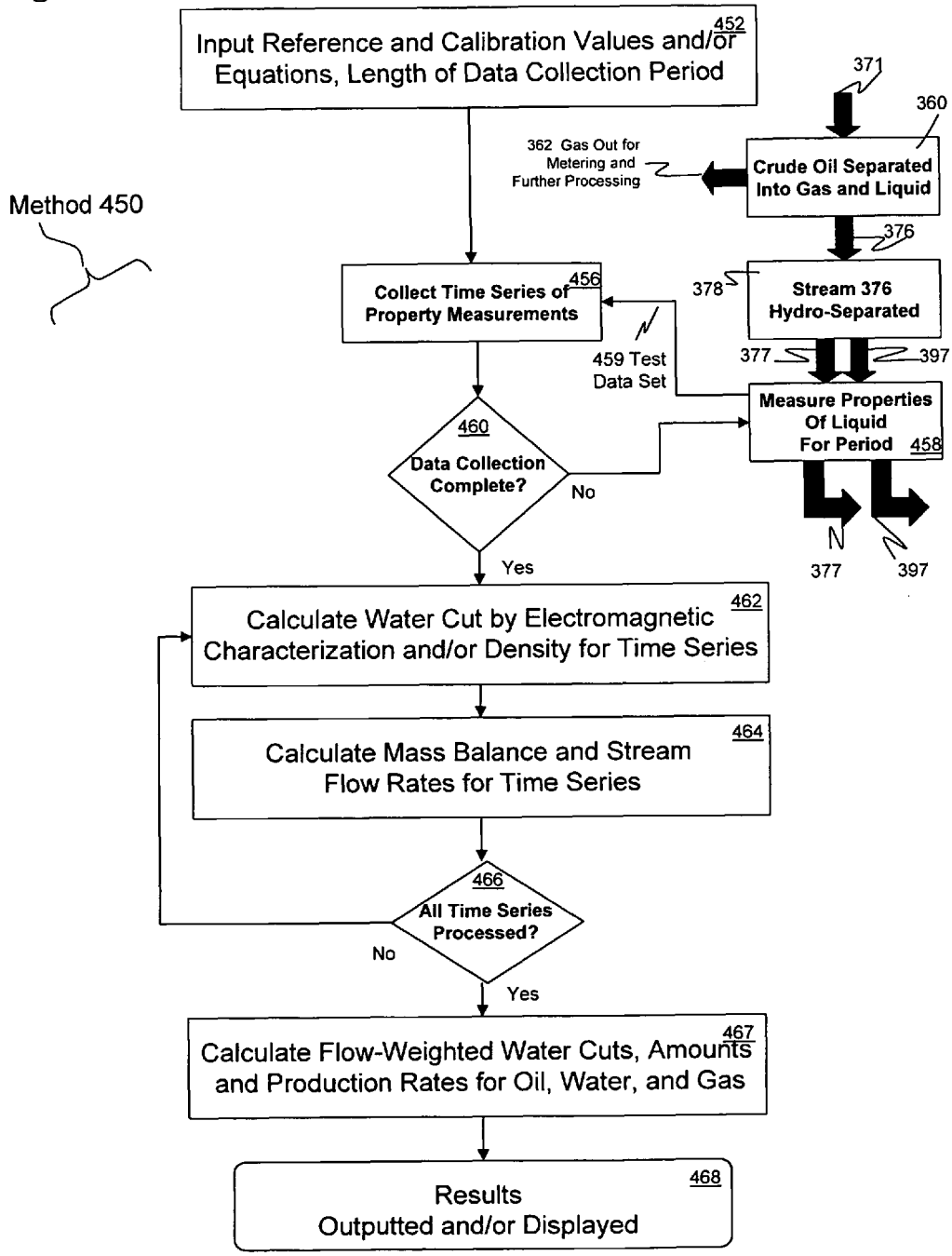
FIG. 4 shows a method, consistent with one embodiment of the present application.

Measuring components 354, 356, 364, 390, 392, 391, and 391A can all or selectively be coupled to flow computer 372 which in one embodiment, performs the method of FIG. 4 and output the results per step 468. In another embodiment, flow computer 372 can transmit or output collected measurements to external system 374 via communications link 396 where the measurements can be stored or the calculations and steps of, in one embodiment, the method of FIG. 4, can be performed and can be out-putted.

FIG. 4 shows method 450 according to one embodiment of the disclosed innovations for measuring the water cut of a high water cut crude petroleum oil stream using hydro-separation consistent with the present application. The method of FIG. 4 can be used, in some embodiments, with the systems of FIG. 1, FIG. 1A, FIG. 2, FIG. 2A, and FIG. 3. For the purpose of the description of the method, and not as a limitation of the present application, the method of FIG. 4 will be described with reference to the system of FIG. 3 and the system of FIG. 2. In one embodiment of the present innovations, known values can be inputted for use by computer or microprocessor system 372 (step 452). In another embodiment, the length of the test time, or data collection period, can be entered (also in step 452). In one embodiment of the present innovations, the method of FIG. 4 can read and collect electromagnetic properties, such as microwave permittivity readings on the less dense fraction liquid, e.g. the oil stream 377 (step 458), including measurements on enough flow rate information on streams 352, 371, 362, 376, 377, 397, and/or 370, or various combinations thereof, to complete the mass balance for system 350.

In one embodiment of the present innovations, the method of FIG. 4 can read and collect physical properties, such as density readings, on the less dense fraction liquid, e.g. the oil-enriched stream 377 (step 458).

All of these values or data 459 can be collected or stored in the memory of the computer or microprocessor system 372, via step 456, and can be used to implement methods of the present innovations, such as the method of FIG. 4. In one embodiment of the present innovations, the values and/or results can be communicated to an external system 374 via link 396 for various operations such as storage, processing, data manipulation, transform development, and correction of raw data via the transforms by implementing the method of FIG. 4 on external system 374. In one embodiment of the present innovations in which the length of a test is inputted, the method can check to see if the test and gathering of data is complete (step 460). If not, the method can repeat, or "loop", by returning to step 458 to read and then step 456 to collect more measurement values. Then, in one embodiment of the present innovations, at the end of, for example, a well production period, as decided by step 460, the method can calculate the water cut by electromagnetic characterization and/or density for each time point using the collected property measurements from step 456 (step 462). In one embodiment of the present innovations, the method can calculate the mass balance and stream flow rates for each time point in the time series in step 464. In one embodiment, the method can determine if all of the data in the time series has been processed to calculate the mass balance and flow rates for each time point (step 466). If not, the method can return to step 462. If all time data points have been processed, in one embodiment of the present innovations, the method can calculate flow-weighted water cuts, total amounts of oil, water, and gas produced, and production rates of each (step 467). In one embodiment of the present innovations, the results are outputted and/or displayed via step 468.

Further, according to a disclosed class of innovative embodiments, there is provided a method for measuring the water content of a multiphase fluid flow stream which can be a water-continuous dispersion, comprising the actions of a) separating, from said flow stream, an oil-enriched fractional stream, b) measuring the fraction of water in said oil-enriched fractional stream, and c) calculating and outputting a measurement of the water content of the original flow stream, based on the result of said measuring action (b) and at least one flow rate measurement, whereby said separating action (a) reduces uncertainty in said measuring action (b).

Further, according to a disclosed class of innovative embodiments, there is provided a method for measuring the water content of a flow stream of a saline water-continuous dispersion of a non-aqueous fluid, comprising the actions of a) separating at least some water from said flow stream, b) measuring the fraction of water downstream from said action (a), and c) calculating and outputting the water content of the original flow stream, based at least in part on said measuring action (b), whereby said separating action (a) reduces uncertainty in said measuring action (b).

Further, according to a disclosed class of innovative embodiments, there is provided a system for measuring the water content of a water-continuous dispersion, comprising a separator in said flow stream, which produces an oil-enriched fractional flow stream, a measurement system which measures the fraction of water in said oil-enriched fractional stream; wherein said measurement system determines and outputs a measurement of the water content of the original flow stream based on said measured fraction of water in said oil-enriched fractional stream and at least one flow rate measurement, whereby said separator reduces uncertainty in the water content measurements.

Further, according to a disclosed class of innovative embodiments, there is provided a system for measuring the water content of a flow stream of a water-continuous dispersion of a non-aqueous fluid, comprising a separator which removes at least some water from said flow stream, a measurement system which electrically measures the fraction of water in said flow stream downstream from said separator, and wherein said measurement system determines and outputs a measurement of the water content of the original flow stream based on the output of said measurement stage and at least one flow rate measurement, whereby said separator reduces uncertainty in the water content measurements.

Further, according to a disclosed class of innovative embodiments, there is provided a system for measuring the water content of a water-continuous dispersion, comprising a separator in said flow stream, which produces oil-enriched and oil-depleted fractional flow streams, a measurement stage which measures the fraction of water in at least one said fractional streams from said separator, a flow stream combination stage which recombines said fractional streams, wherein said measurement system determines and outputs a measurement of the water content of the original flow stream based on said the output of said measurement stage, whereby said separator reduces uncertainty in the water content measurements.

Further, according to a disclosed class of innovative embodiments, there is provided a system for measuring the water content of a multiphase fluid flow stream, comprising means for separating hydrocarbon-enriched and hydrocarbon-depleted fractional streams from the flow stream, means for measuring water/oil ratio in at least one said fractional stream, and means for calculating and outputting the hydrocarbon content of the original flow stream, based on the result of said measuring means.

MODIFICATIONS AND VARIATIONS

As will be recognized by those skilled in the art, the innovative concepts described in the present application can be modified and varied over a tremendous range of applications, and accordingly the scope of patented subject matter is not limited by any of the specific exemplary teachings given. It is intended to embrace all such alternatives, modifications and variations that fall within the spirit and broad scope of the appended claims.

The methods and systems of the present application can operate across a wide range of processing situations and conditions. One of ordinary skill in the art, with the benefit of this disclosure, will recognize the appropriate use of the methods and systems for a chosen application of a given or dynamic set of operating parameters, including process pressure, process temperature, process flow rate, multiphase fluid composition, aqueous phase composition, non-aqueous-phase composition, presence of condensible gases, presence of non-condensible gases, use of flow stream conditioning operations prior to characterization, flow stream pipe location, measurement apparatus location, ambient temperature, or other conditions, or various combinations thereof.

Optionally, the methods and systems of the present application can be configured or combined in various schemes. The combination or configuration depends partially on the required measuring precision and accuracy and the operational envelope of the process. One of ordinary skill in the art, with the benefit of this disclosure, will recognize the appropriate combination or configuration for a chosen application.

Optionally, the methods and systems of the present application can also take the temperature and pressure of flow streams, the density of gas streams, liquid levels in separators, oil-water interfaces in hydro-separators, and any flags such as separator level out of range which can define the reliability of the data or provide variables to use for analysis, or various combinations thereof. One of ordinary skill in the art, with the benefit of this disclosure, will recognize the appropriate additional measurements that can be beneficially flagged for a chosen application.

Optionally, such measurements taken by the methods and systems of the present application can also be sent to the external computer or microprocessor system 374 for processing. For example, if the gas density exceeds a certain amount, this fact can be used to flag improper data due to liquids carrying over into the gas from the separator during a system upset. Liquid density having a large standard deviation beyond a preset level can be used for the same determination. This can be due to gas carry under into the liquids, which would make the liquid density very noisy.

Optionally, the methods and systems of the present application can use two or more hydro-separators in either series or parallel installation to achieve a desired degree of separation or throughput.

Optionally, the methods and systems of the present application can use pumps to boost the pressure of the multiphase flow stream entering the hydro-separator.

Optionally, multiphase fluid temperature compensation can be employed used to adjust for shifts in temperature using reference data sets relating temperature change to total fluid density change, or curves fitted to such reference data. Optionally, because the thermal expansion of an oil continuous dispersion is generally different than the thermal expansion of a water-continuous dispersion, different reference data sets or curves fitted to such data sets can be employed. Optionally, because the coefficient of thermal expansion for aqueous solutions and non-aqueous solutions differ, calculation routines can use the measured first phase fraction to better adjust for such temperature shifts. One of ordinary skill in the art, with the benefit of this disclosure, will recognize the appropriate systems to employ for such temperature compensation methods.

Optionally, examples of suitable hardware which can be fully or partially modified to fully or partially embody the methods and systems of the present application include those that are commercially available from Phase Dynamics of Richardson, Tex.

Optionally, the systems of the present application may not be located in a pipe or conduit. In one class of embodiments, the physical property measuring component and the electrical property measuring component may be located via an insertion installation in a vessel such as a storage tank, mixing tank, accumulator, separator, liquid-liquid contactor, or other processing device for which a multiphase fluid measurement is required. One of ordinary skill in the art, with the benefit of this disclosure, will recognize the appropriateness of the methods and systems of the present application for a chosen application.

Optionally, the systems of the present application can include a sampling port for comparison of the on-line determinations of first phase with an off-line determination.

Optionally, the methods of the present application can also be embodied in a set of instructions that can be used on a general purpose desktop or laptop computer or microprocessor system, such as external system 374. The set of instructions can comprise input instructions that receives data from flow computer or microprocessor system 372. Similarly, the input instructions can accept instructions from a user via one or more input devices, such as a keyboard, mouse, touchpad, or other input device. The instructions can also implement the methods of the present invention or any part thereof to generate, for example, an updated transform for the calculation of first phase fraction by either the density method or the electromagnetic characterization method. The instructions can cause the computer or microprocessor system to display information, such as the results of the methods of the present invention, to a user, through a display monitor, printer, generated electronic file, or other such device. The instructions can also cause the computer or microprocessor system to transmit the results to a distant user via modem, cable, satellite, cell link, or other such means. For such digital communications, RS-422 or RS-485 can optionally be used to allow links from flow computer or microprocessor system 372 or external system 374 to multiple external units. Optionally, a 4-20 milliamp analog output signal can be used to allow external processing of the system measurements.

Optionally, the methods of the present invention can also be embodied in a computer readable medium.

Optionally, the disclosed ideas are used to estimate water phase fraction and the oil phase fraction in a multiphase flow stream which is subjected to a conventional 2-phase or 3-phase separator.

Optionally, the disclosed ideas are used at the wellhead of (or slightly downstream from) a producing hydrocarbon well by first removing essentially any non-condensible gas fraction contained in crude petroleum emerging from the wellhead or from a gas-liquid separator, before entering the separation process which produces an enriched oil-phase.

Optionally, the disclosed ideas can be used in conjunction with the methods of U.S. patent application Ser. No. 11/499,391 and U.S. Pat. Nos. 7,457,714 and 7,334,450, which are hereby all incorporated by reference.

Optionally, the disclosed ideas are used to estimate the water phase fraction and the oil phase fraction in a multiphase flow stream which is subjected to a separation process which has individual flow meters to measure the outlet flow rates of the oil-enriched phase and the water-enriched phase, or as an alternative, individual flow meters to measure the flow rates of the oil-enriched phase and the inlet multiphase mixture of crude oil and water.

Optionally, the disclosed ideas are used to estimate the water phase fraction and the oil phase fraction in a multiphase flow stream which is subjected to a separation process which has a flow meter to measure the flow rate of the inlet multiphase mixture of crude oil and water and the outlet flow rates are calculated based on fluid flow calculations using information such as pressures, flow conduit dimensions, and flow conduit characteristics.

None of the description in the present application should be read as implying that any particular element, step, or function is an essential element which must be included in the claim scope: THE SCOPE OF PATENTED SUBJECT MATTER IS DEFINED ONLY BY THE ALLOWED CLAIMS. Moreover, none of these claims are intended to invoke paragraph six of 35 USC section 112 unless the exact words "means for" are followed by a participle. The claims as filed are intended to be as comprehensive as possible, and NO subject matter is intentionally relinquished, dedicated, or abandoned.

What is claimed is:

1. A method for measuring the water content of a multiphase fluid flow stream which can be a water-continuous dispersion, comprising the actions of:

a. separating, from said flow stream, an oil-enriched fractional stream;
b. measuring the fraction of water in said oil-enriched fractional stream; and
c. calculating and outputting a measurement of the water content of the multiphase fluid flow stream, based on the result of said measuring action (b) and at least one flow rate measurement,
whereby said separating action (a). reduces uncertainty in said measuring action (b).

2. The method of claim 1, wherein said measuring in action (b) is an electromagnetic characterization of said oil-enriched fractional stream.

3. The method of claim 1 wherein essentially any gas phase is removed from the multiphase fluid flow stream before said action (a) is conducted, wherein the amount of gas is measured; and wherein the amount of oil, water, and/or gas in the original flow stream per unit of time is measured and outputted.

4. The method of claim 1, wherein said oil-enriched fractional stream is oil-continuous.

5. A system for measuring the water content of a water-continuous dispersion, comprising:

a separator in said dispersion, which produces an oil-enriched fractional flow stream; and a measurement system which measures the fraction of water in said oil-enriched fractional stream, wherein said measurement system determines and outputs a measurement of the water content of the continuous dispersion based on said measured fraction of water in said oil-enriched fractional stream and at least one flow rate measurement, whereby said separator reduces uncertainty in the water content measurements.

6. The system of claim 5, wherein essentially any gas phase is removed from the multiphase fluid flow stream before the stream enters said separator; wherein the amount of gas removed is measured; and wherein the amounts of oil, water and/or gas in the original flow stream per unit of time is calculated and outputted.

7. The system of claim 5, wherein said measurement system includes an electromagnetic property measuring device which can measure the water content of a multiphase fluid.

* * * * *